United States Patent [19]

Combs

[11] Patent Number: 5,667,510
[45] Date of Patent: Sep. 16, 1997

[54] JOINT FIXATION SYSTEM AND METHOD

[76] Inventor: C. Robert Combs, 708 Turf Ct., Lexington, Ky. 40502

[21] Appl. No.: 510,721

[22] Filed: Aug. 3, 1995

[51] Int. Cl.[6] .................................................. A61B 17/56
[52] U.S. Cl. ............................. 606/86; 606/69; 606/73; 606/85; 606/87
[58] Field of Search .................... 606/67, 62, 63, 606/65, 69, 72, 73, 86, 87, 90, 96, 105, 80, 82, 84, 177

[56] References Cited

U.S. PATENT DOCUMENTS

| | | | |
|---|---|---|---|
| 3,779,239 | 12/1973 | Fischer et al. | 606/63 |
| 3,986,504 | 10/1976 | Avila | 606/63 |
| 4,036,236 | 7/1977 | Rhodes, Jr. | 606/177 |
| 4,204,531 | 5/1980 | Aginsky | 606/63 |
| 4,275,717 | 6/1981 | Bolesky | 606/63 |
| 4,453,539 | 6/1984 | Raftopoulos et al. | 606/63 |
| 4,487,203 | 12/1984 | Androphy | 606/88 |
| 4,502,483 | 3/1985 | Lacey | 606/100 |
| 4,655,119 | 4/1987 | Steffee | 606/61 |
| 4,708,133 | 11/1987 | Comparetto | 606/82 |
| 4,718,413 | 1/1988 | Johnson | 606/82 |
| 4,776,330 | 10/1988 | Chapman et al. | 606/64 |
| 4,973,332 | 11/1990 | Kummer | 606/65 |
| 4,973,333 | 11/1990 | Treharne | 606/77 |
| 5,030,219 | 7/1991 | Matsen, III et al. | 606/53 |
| 5,041,116 | 8/1991 | Wilson | 606/65 |
| 5,049,149 | 9/1991 | Schmidt | 606/87 |
| 5,176,685 | 1/1993 | Rayback | 606/87 |
| 5,250,050 | 10/1993 | Poggie et al. | 606/79 |
| 5,350,382 | 9/1994 | Armstrong | 606/87 |

FOREIGN PATENT DOCUMENTS 453570  6/1968  Germany.

*Primary Examiner*—Michael Buiz
*Assistant Examiner*—David O. Reip
*Attorney, Agent, or Firm*—King and Schickli

[57] ABSTRACT

A method and related instruments are provided for the preparation, stabilization and fusion of the middle and distal phalanx bones in the finger. The method includes the steps of cutting the head of the middle phalanx to form one side of a miter joint and drilling a guide bore through both bones. The adjacent end of the distal phalanx is smoothed using a rotary disk with a center guide post to create the opposing side of the miter joint. A fixation plate is secured to the top of the finger and includes a positioning tube that extends into the guide bore. A screw assembly extends through the tube and into the bones to provide a compressive force across the miter joint. The preferred apparatus includes a combination drill template/saw guide for drilling the guide bore and cutting the middle phalanx, a rotatable disk for smoothing the distal phalanx and a screw assembly having spirally expanding strands at its distal end for anchoring the assembly in the distal phalanx. A tool kit including these instruments is also provided.

16 Claims, 3 Drawing Sheets

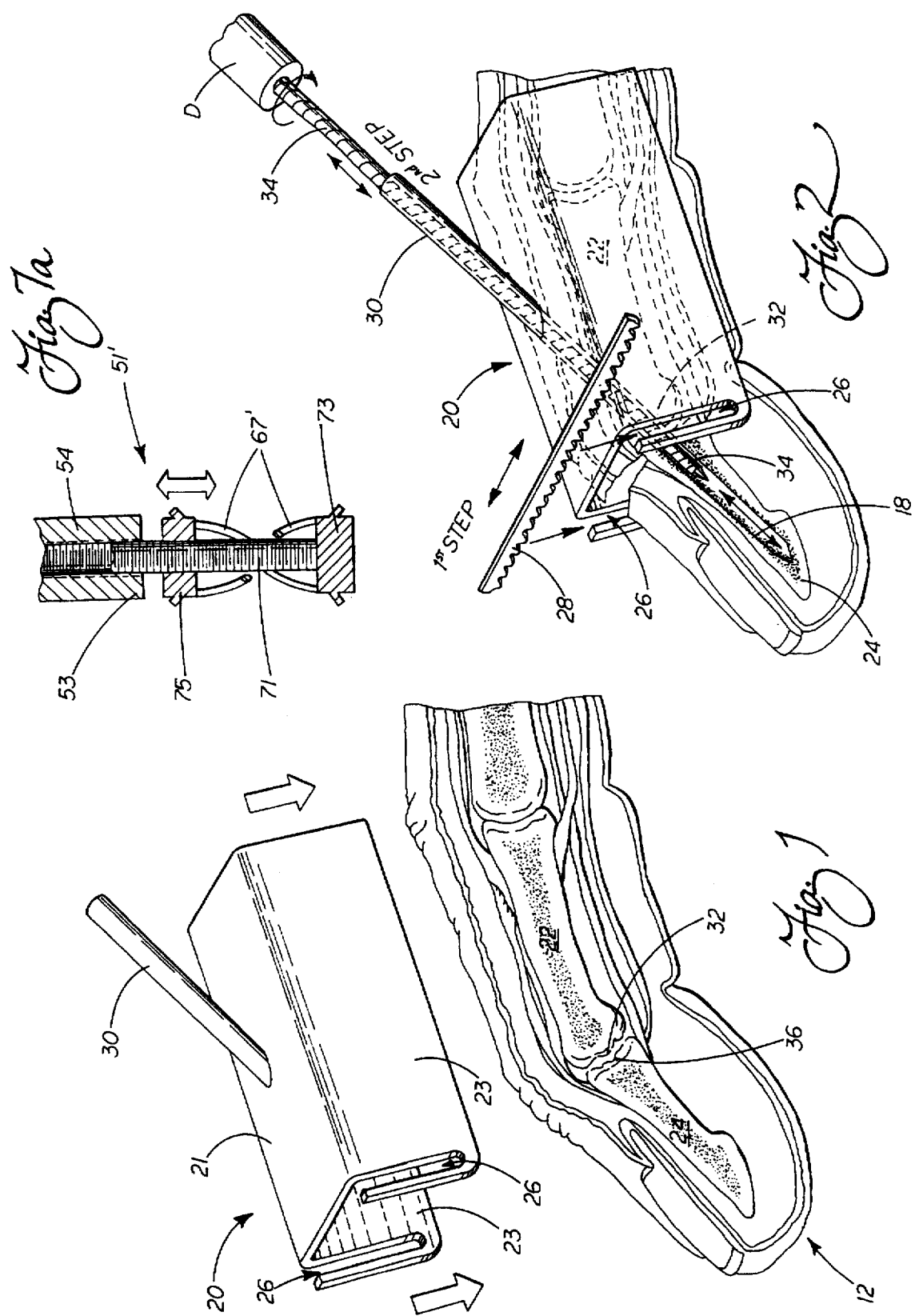

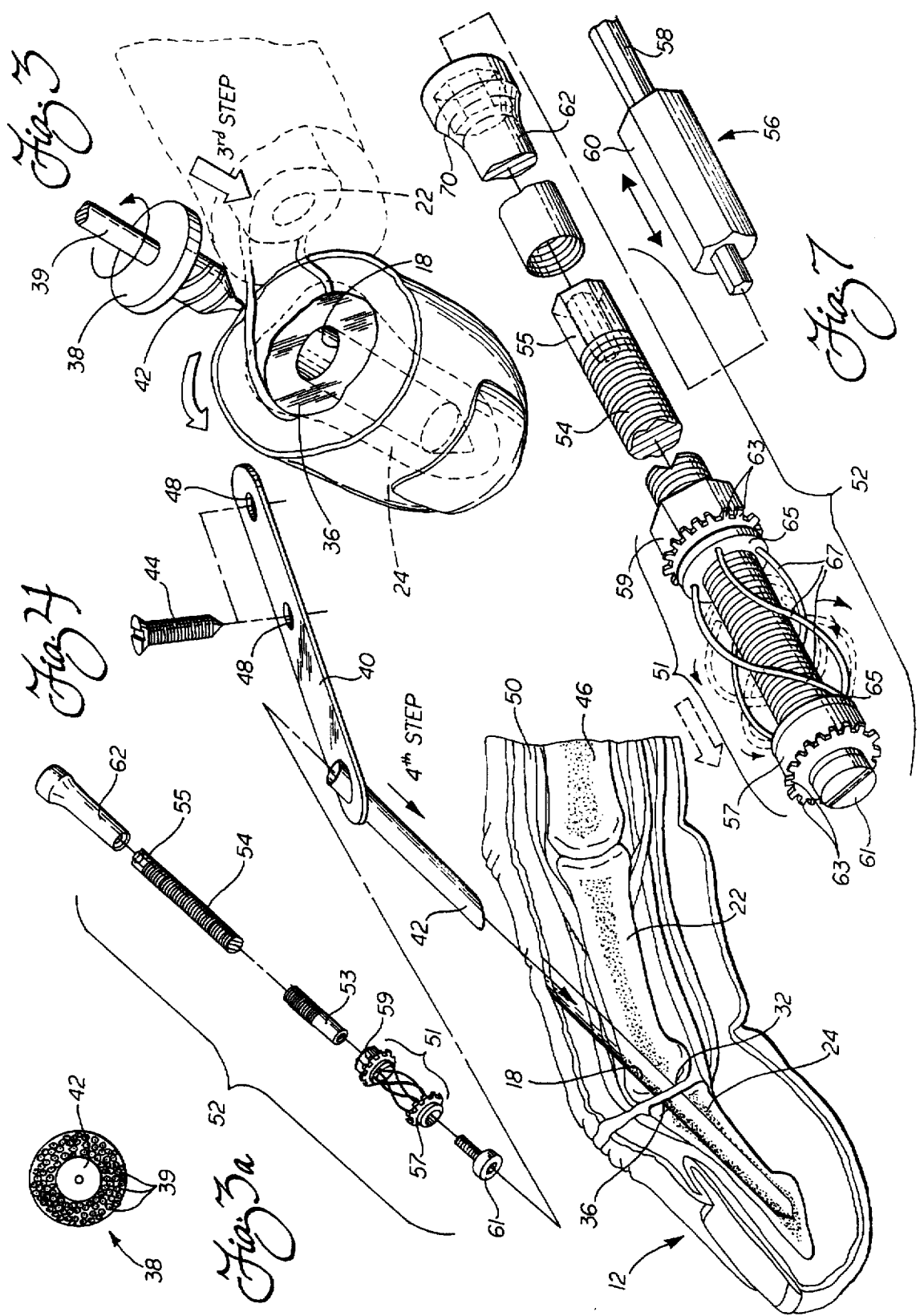

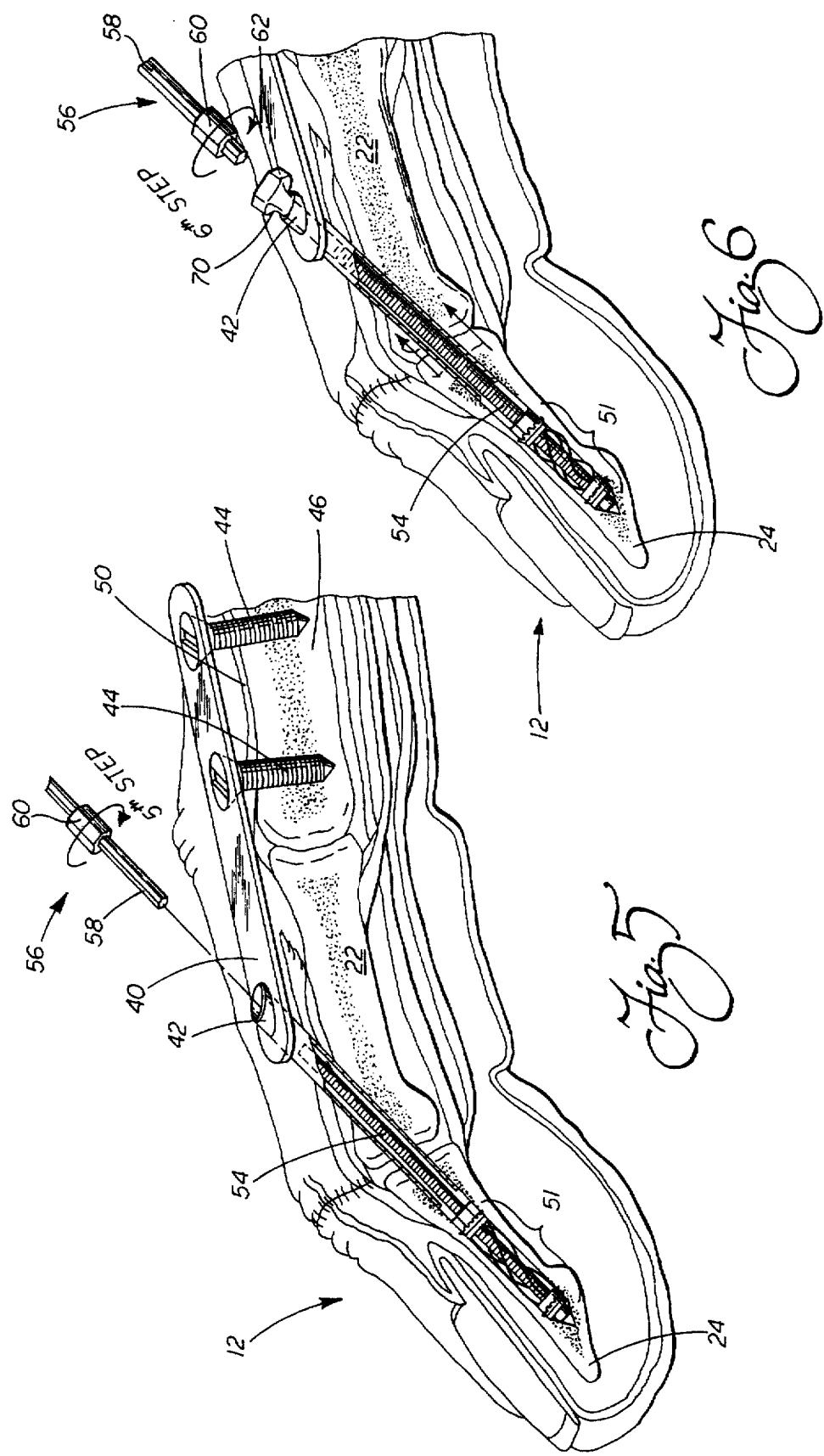

JOINT FIXATION SYSTEM AND METHOD

TECHNICAL FIELD

The present invention relates generally to a method and corresponding system for repairing damaged joints; and more particularly, to an improved method and a related kit and instruments for preparing and stabilizing a joint in the finger for fusion.

BACKGROUND OF THE INVENTION

Various methods and apparatus are known for fixating a damaged bone joint or a fracture to allow fusion to take place. In a typical procedure, the opposing bone surfaces of the joint or fracture are first made planar by sawing and/or smoothing. Next a bore is drilled through the joint or fracture and a compression screw is then inserted into the bore and a compressive force is applied to the joint or fracture to allow the fusion process to occur.

Especially with the small bones and joints of the finger, the integrity of a fused joint is often largely dependent upon the skill of the surgeon in accurately positioning and aligning the cutting and drilling instruments to make properly angled cuts and bores. Although it is well known for a surgeon to use a template or guide to achieve precise angles in certain cutting and drilling procedures, the techniques and instruments of the prior art are ill-suited for fusion procedures on the small bones of the finger.

The fusion methods of the prior art teach the use of an individual template for positioning a saw blade to make a properly angled cut and a separate drill guide for drilling a guide bore. As two separate instruments are used, each template or guide must be individually aligned and secured before each step, increasing both the time of the surgery and the chance of misalignment. Furthermore, most of the prior art templates and guides are designed for fusion procedures on large joints and bones, such as the femur, and none are specifically designed for use on the much smaller phalanxes of the fingers. Examples of prior art saw guides and separate drill templates are U.S. Pat. No. 5,250,050 to Poggie et al. and U.S. Pat. No. 5,176,685 to Rayhack.

It is also well known to use a fixation plate and a corresponding compression instrument, such as a screw, to stabilize and compress the joint or fracture together to allow it to fuse. The fixation plate is typically affixed directly to the bone to be repaired and the compression screw is inserted through an aperture in the plate and into the guide bore drilled through the damaged joint or fracture. The screw is anchored in the distal end of the joint/fracture and engages the fixation plate to create a compressive force. Examples of typical fixation plates and compression screws are shown in U.S. Pat. No. 4,776,330 to Chapman et al. and U.S. Pat. No. 5,041,116 to Wilson.

However, like the prior art templates and guides, the prior art fixation plates and compression screws are designed to be used on large bones and joints and are ill-suited for use on the smaller bones and joints of the finger. In particular, the fixation plates of the prior art are designed for subcutaneous fixation and include bone screws that are randomly placed along the plate for direct engagement with the bone. These designs are not suited for attachment to the top of a finger, as the bone screws will damage the underlying extensor digitorum tendon.

The compression screws of the prior art are also primarily designed for use on fractures as opposed to damaged joints, in addition to being suitable only for large diameter bones. Many of the prior art designs are comprised of multiple concentric screws and/or sleeve assemblies that must fit into a single bore that is drilled through the fracture. For example, the compression screw assembly taught in the '330 patent to Chapman et al. requires that a separate expansion sleeve, plunger, insertion rod and guide wire all be inserted into the fractured bone. Although well-suited for use on a fractured femur head, the numerous components and wide profile of this design makes the assembly much too cumbersome to be used on the small diameter bones of the finger. Additionally, the numerous components of this design require multiple steps for installation, thereby increasing the overall time and complexity of the fusion procedure.

Thus, as demonstrated by the limitations of the prior art, there is a need identified for a joint fixation system and method that allows the surgeon to accurately and efficiently perform fusion procedures on joints in the fingers. In addition, a related tool kit containing instruments that are specifically designed for fusion procedures on the small bones in the fingers is desired.

SUMMARY OF THE INVENTION

Accordingly, it is a primary object of the present invention to provide a novel and improved joint fixation system, method and related kit and instruments that are particularly adapted for use on bones in the fingers and include concepts and features that are designed to overcome the limitations of the prior art.

Another object of the present invention is to provide a joint fixation system and method wherein consistent precision and accuracy are achieved in drilling a guide bore through the joint and in cutting/smoothing the opposing faces of the joint to form planar surfaces for optimal fusion.

It is another object of the present invention to provide a joint fixation system and method that minimizes the number of steps and the required time for the fusion procedure.

It is still another object of the present invention to provide a novel and improved instrument kit for preparing, stabilizing and fusing a bone joint in the finger.

It is yet another object of the present invention to provide a combination template having drill and saw guides to allow both a properly angled guide bore and a sheer cut to be made without repositioning the template.

It is still another object of the present invention to provide a fixation plate that is specifically adapted for use on the finger and includes carefully positioned bone screw apertures that avoid damaging underlying tendons.

It is yet another object of the present invention to provide a compression screw assembly having a simple, small-diameter design that is specifically adapted for insertion into the small bones of the finger, and having a releasable anchor means at its distal end, and further including helically expanding flexible strands for improved engagement with the surrounding bone.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, a novel and improved joint fixation system, method and related instrument kit are provided that are particularly adapted for fusion procedures on the bones of the fingers, and more specifically on the joint between the middle and distal phalanxes. As described in greater detail below, the improved method includes preparatory steps in which the articulating bone surfaces are cut, a guide bore is drilled into the bones and smoothed for optimal fusion. A fixation plate/positioning tube is then affixed to the top of the finger with the tube extending into the guide bore. A compression screw assembly extends into the guide bore through the tube, and is then tightened against the fixation plate to provide the desired compressive force to the joint.

In order to most efficiently carry out these steps, the present invention includes an instrument kit containing a number of specialized instruments that are particularly adapted for use on the small bones of the fingers. For the initial cutting and drilling steps, the invention contemplates using a single combination template for both procedures.

Specifically, the template comprises an elongated inverted channel that includes dual saw guide slots at its front end. The slots have parallel spaced edges and are positioned to align a reciprocating saw blade to cut the rounded head of the middle phalanx. In the first step of the method, the saw blade is thus lowered into the slots for guiding and a clean controlled cut is made to create a smooth and substantially vertical planar surface.

The elongated drill guide cylinder of the template extends upwardly at an angle from the upper face of the template. In the second step of the method, the cylinder guides a rotary drill bit to make a guide bore at the required angle through the head of the middle phalanx and longitudinally into the distal phalanx. Preferably, the positioning of the slots and the drill guide cylinder is coordinated to allow both sawing/ smoothing and drilling steps to be performed without realigning the template on the finger.

Advantageously, using this single combination template to guide both the cutting and drilling steps provides increased accuracy to insure that the desired matching surface and bore angles are achieved. Also, by eliminating the need for installing a second guide or template, the substantial reduction in surgery time is assured.

In the third step of the method, the distal phalanx is dislocated to one side and the base of the distal phalanx is smoothed to create a planar surface that is parallel to, and substantially mates with the previously cut and smoothed head of the middle phalanx, thereby forming a miter joint for optimal fusion. To form this surface, the tool kit includes a substantially flat rotary disk with randomly spaced cutting protrusions on its working surface. To properly position the disk above the distal phalanx, a center guide post extends from the center of the working surface and fits closely in the guide bore as the rotating disk engages the bone. In this manner, the surgeon is assured of creating a planar surface that is as near a perfect match for the head of the middle phalanx as possible.

In the fourth step of the method of the present invention, an elongated fixation plate is affixed to the top of the middle phalanx of the finger by self-tapping bone screws that extend through tapered apertures in the plate. The apertures are carefully positioned and installation carefully monitored to avoid damaging the underlaying tendons in the finger. The plate also includes a positioning tube that depends downwardly at an angle from the front portion of the plate. The positioning tube has an outside diameter that is smaller than, but snugly fits the inside diameter of the guide bore to allow the tube to be easily inserted and feed securely in the bore.

When fully inserted, the tube extends past the mitered joint and into the distal phalanx. Advantageously, the tube keeps the bones properly aligned and helps stabilize the joint for proper healing. The tube also protrudes slightly above the plate surface to provide a stop for the compression screw assembly, described immediately below.

In the fifth step of the method, an elongated compression screw assembly is inserted through the positioning tube and anchored in the distal portion of the guide bore. When fully inserted, the proximal end of the screw assembly remains recessed inside the positioning tube and below the skin level. Advantageously, this protects the screw assembly from inadvertent outside contact that could disrupt the healing process.

The screw assembly includes a unique releasable anchor means that is particularly well-suited for use with small diameter bones, such as the phalanxes. In the preferred embodiment of the anchor means, a plurality of spiraling stands is compressed between a rotatable end collar and a threaded lead nut. Both the end collar and the lead nut include radially extending prongs around their periphery that engage the surrounding ossiferous surface of the guide bore. Preferably, the prongs embody sufficient flexibility to allow longitudinal insertion and withdrawal movement of the screw assembly and the individual expansion nut into and from the guide bore, while simultaneously providing sufficient friction to prevent the nut and/or collar from rotating due to the torque from the threads of the rotating screw shaft.

Two flat washers serve as end plates between the opposing faces of the lead nut and the end collar. Flexible and relatively stiff metal strands extend longitudinally between the washers in overlapping helices and provide a biasing force that presses each washer against the adjacent lead nut or collar. With this construction, rotation of the screw in the appropriate direction advances the lead nut toward the collar, causing the strands to spirally/helically expand outwardly and engage the surrounding bone. Advantageously, the overlapping spiral configuration of the strands allows for stable and secure contact with the surrounding bone along substantially the entire length of each strand, thereby firmly anchoring the screw assembly in the distal phalanx. Expansion of the strands is achieved by simply rotating the screw shaft with an Allen tool that engages a hexagonal aperture in the proximal end of the shaft. A removable threaded cap screw in the distal end of the screw shaft allows for convenient selection/replacement of the anchor means.

In an alternative "narrow-profile" embodiment of the anchor means, an extension screw with a fixed end collar and a non-threaded lead nut is threaded into a threaded hole in the distal end of the main screw assembly shaft. The non-threaded lead nut rotates freely about the smaller extension screw shaft and abuts the distal end of the main screw shaft. As the main shaft is rotated, it moves down the extension screw and presses the expansion nut towards the end collar to expand the enclosed strands outwardly. Advantageously, the expansion nut and end collar of this "narrow-profile" embodiment have outside diameters no wider than the main shaft, thereby allowing this assembly to be used in extremely small bones with guide bores only slightly larger than the main screw shaft.

Once the compression screw assembly is anchored in the distal phalanx, the sixth and final step of the method uses an elongated shoulder nut that is threaded onto the proximal end of the screw shaft. By tightening the shoulder nut against the protruding lip of the tube, the screw assembly tends to be drawn outwardly from the tube, thus providing the desired compressive force to the joint. Preferably, the kit also includes a combination Allen driver tool that both operates the anchor means by rotating the screw shaft and tightens the shoulder nut to provide the compressive force.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modifications in various, obvious aspects all without departing from the invention. Accordingly, the drawings and descriptions will be regarded as illustrative in nature and not as restrictive.

BRIEF DESCRIPTION OF THE DRAWINGS

FIG. 1 is a perspective view of the combination template of the present invention showing the template being installed over a damaged joint between a middle and distal phalanx bone in a finger.

FIG. 2 is a perspective view of the first and second steps of the present invention showing a reciprocating saw blade being guided by the slots in the template to cut the head of the middle phalanx, and showing a rotary drill bit being inserted into and retracted from the drill guide cylinder to make the drill guide bore through the middle and distal phalanx.

FIG. 3 is a perspective view of the third step of the present invention showing the distal phalanx dislocated to one side and a rotatable smoothing disk being used to smooth the base of the distal phalanx. FIG. 3a is an end view of the working surface of the smoothing disk of FIG. 3 showing the middle guide post and the raised cutting protrusions randomly spaced on the surface.

FIG. 4 is an overall perspective view illustrating the fixation plate and the preferred embodiment of the compression screw assembly in exploded relationship, and showing by dash/dot line a representation of the fourth step of the present invention in which the positioning tube and the screw assembly are inserted into the guide bore.

FIG. 5 is a cut away partial view showing the fixation plate secured to the proximal phalanx with bone screws and illustrating the fifth step of the present invention in which the compression screw shaft is rotated to expand the anchor means at the distal end of the screw assembly.

FIG. 6 is a cut away partial view of the sixth step of the present invention in which an elongated shoulder nut is threaded onto the compression screw assembly to tend to draw the screw assembly outwardly from the positioning tube and compress the joint together for fusion.

FIG. 7 is an overall perspective view of the compression screw assembly with the preferred embodiment of the releasable anchor means, the shoulder nut and the combination driver tool, showing by action arrow and dashed outline the expansion of the releasable anchor means.

FIG. 7a is an enlarged cross-sectional view of the alternate embodiment of the releasable anchor means.

Reference will now be made in detail to the present preferred embodiment of the invention, an example of which is illustrated in the accompanying drawings.

DETAILED DESCRIPTION OF THE PREFERRED EMBODIMENT

Reference is now made generally to FIGS. 1–7 which illustrate an improved joint fixation system and method, including a related instrument kit comprising novel and improved instruments that are used to perform the method. The system/method and corresponding kit are particularly adapted for use in fusion procedures on joints in the hand, and more specifically in fusing the joint between the middle and distal phalanges in a finger.

With reference now to FIGS. 1 and 2, the improved fusion method of the present invention begins with a preparatory step in which the damaged surface of the middle phalanx 22 (next to distal phalanx 24) is cut and smoothed for fusion. Next, a guide bore 18 is drilled through the joint and into the distal phalanx 24. To assist the surgeon in performing the cutting and drilling steps, a combination template, generally designated by the reference numeral 20, is positioned over the joint and is lowered onto the finger 12 in the direction of the action arrows in FIG. 1. At the front end of the template 20 are parallel saw guide slots 26 that are open at their top end to receive a reciprocating saw blade 28. The template 20 also includes an elongated drill guide cylinder 30 that extends upwardly at an angle from the top horizontal surface 21 of the template 20.

As shown in FIG. 2, with the template 20 affixed to the top of the finger by a C-clamp or other suitable means (not shown), the first step of the method involves lowering the reciprocating saw blade 28 into and along the slots 26 to make a flat, substantially vertical cut from the head 32 of the middle phalanx 22. Preferably, the edges of the slot 26 are spaced to allow the reciprocating movement of the saw blade 28 while still providing lateral guidance to insure that a planar and properly angled cut is made.

In the second step of the method, an elongated drill bit 34 is chucked in a hand-held rotary drill D and is guided by the cylinder 30 to drill the guide bore 18. The cylinder 30 is positioned to specifically drill the bore 18 at an angle through the head 32 of the middle phalanx 22 and longitudinally into adjacent base 36 of the distal phalanx 24. Advantageously, the guide cylinder 30 insures that the guide bore 18 is drilled substantially straight through the center of the joint and into the center of the distal phalanx 24.

In an important aspect of the present invention, the use of the combination template 20 provides markedly improved accuracy in the cutting and drilling steps as compared to performing these steps with prior art methods or instruments. Additionally, the dual function of the combination template 20 eliminates the need for a second template or guide. Furthermore, in the preferred method, the cutting and drilling steps are both performed without repositioning the template 20, thereby reducing the time required for the overall procedure, and always insuring a proper relationship between the cutting and drilling angles.

With reference now to FIG. 3, the third step begins with dislocating the distal phalanx 24 to one side to expose the base 36 of the bone. Using a rotatable smoothing disk 38, the base 36 is then smoothed to form a flat and planar surface that is parallel to the corresponding end 32 of the middle phalanx 22.

As shown in FIG. 3a, the working surface of the smoothing disk 38 includes randomly spaced cutting protrusions 39. Extending from the center of the working surface is a cylindrical guide post 43 that fits closely into the guide bore 18. The guide post 43 centers the smoothing disk 38 above the base 36 to insure that a planar surface is formed that is parallel to the corresponding, mating head 32 of the middle phalanx 22. As best seen in FIG. 4, the opposing head and base 32, 36 form a miter joint that allows for complete surface area contact between the bones for optimal knitting.

With continued reference to FIG. 4, in the fourth step of the method a fixation plate 40 with a downwardly angled positioning tube 42 is affixed to the top of the finger 12, with the tube 42 extending into the guide bore 18. The plate 40 is affixed to the finger 12 by self-tapping bone screws 44 that are advanced into the proximal phalanx 46 (see FIG. 5). Preferably, the bone screw apertures 48 in the plate 40 are carefully positioned to avoid damaging the underlying extensor digitorum tendon 50 that runs above the proximal phalanx 46.

The positioning tube 42 depends downwardly at a fixed angle from the front portion of the fixation plate 40 and into the guide bore 18. The tube 42 also protrudes slightly above the surface of the plate 40 to act as a stop for a compression screw assembly, generally designated by the reference numeral 52 and described in more detail below.

Once the fixation plate 40 is affixed to the top of the finger 12, an elongated compression screw assembly 52 is inserted through the positioning tube 42 until it bottoms in the distal end of the guide bore 18. As best seen in FIG. 5, when fully inserted the screw shaft 54 remains recessed inside the positioning tube 42.

As described in greater detail below, the compression screw assembly 52 includes a releasable anchor means 51 at its distal end for securing the screw inside the guide bore 18.

With the screw assembly 52 fully inserted, the fifth step of the method involves expanding the anchor means 51 at the distal end of the screw to secure the screw assembly 52 in the distal phalanx 24. As illustrated in FIG. 5, a combination tool 56 includes an inner Allen driver 58 that extends into the positioning tube 42 to engage and rotate the proximal end of the screw shaft 54. This action in turn causes the anchor means 51 to expand and secure the screw assembly 52 in the distal phalanx 24. With the screw assembly 52 firmly anchored in the distal phalanx 24, the sixth and final step involves inserting an elongated hollow shoulder nut 62 into the positioning tube 42 and threading the nut 62 onto the screw shaft 54. As shown in FIG. 6, the larger or outer Allen head driver 60 of the tool 56 that slides on the inner driver 58 and engages a mating hexagonal aperture in the shoulder nut 62 to rotate the shoulder nut. As the shoulder nut 62 is advanced down the screw shaft 54, the tapered head 70 of the shoulder nut 62 engages the outer lip of the positioning tube 42. Further rotation of the shoulder nut 62 advances the screw shaft 54 outwardly from the positioning tube 42, thereby pulling the base 36 of the distal phalanx into compressive engagement with the head 32 of the middle phalanx 22. Advantageously, the middle and distal phalanges 22, 24 are now in a stable, compressive engagement that creates optimal conditions for the fusion and healing processes to occur.

The related instrument kit that is provided for carrying out the above-described method includes the combination template 20 having both drill and saw guides. As shown in FIG. 1, the template 20 comprises a horizontal upper face 21 and parallel sides 23 depending downwardly at right angles. At the front end of the template 20 are dual vertical slots 26 that are formed in the parallel sides 23. The slots 26 are open at their top end to receive a reciprocating saw blade 28. Preferably, the spaced edges of the slots 26 allow free longitudinal movement of the blade 28 while simultaneously restricting lateral movement of the blade 28 to insure a straight and accurate cut.

On the upper surface 21 of the template 20, an elongated drill guide cylinder 30 extends upwardly at an angle toward the rear end of the template 20. As shown in FIG. 2, the kit also includes an elongated drill bit 34 that includes a shank (not shown) for chucking in a hand-held rotary drill D. The inner diameter of the cylinder 30 is only slightly larger than the outer diameter of the drill bit 34 to smoothly guide the bit 34 in drilling the guide bore 18. The angle of the guide cylinder 30 insures that the guide bore 18 travels through the middle phalanx 22 and into the center of the distal phalanx 24. Preferably, the placement of the slots 26 and the guide cylinder 30 on the template 20 is coordinated to allow both drilling and sawing steps to be performed without unclamping and repositioning the template 20. In this manner, the template 20 allows two separate steps in the fusion procedure to be accurately performed with a minimal amount of preparation and alignment.

To smooth the head 32 of the distal phalanx 24, the kit includes a substantially flat rotatable disk 38 with randomly-spaced cutting protrusions 39 on its working surface. As shown in FIGS. 3 and 3a, the disk 38 includes a guide post 42 that extends from the center of the working surface and has a diameter slightly less than the inside diameter of the guide bore 18. Advantageously, the guide post 42 centers the disk 38 over the distal phalanx 24 to assist the surgeon in smoothing the bone into a flat, planar surface that is parallel to the opposing head 32. The disk also includes a shank 39 that extends from the rear of the disk 38 for securement in the chuck of a hand-held rotary drill (not shown).

As illustrated in FIG. 4, the kit also includes an elongated fixation plate 40 with a depending positioning tube 42 affixed at one end. The plate includes tapered bone screw apertures 48 that receive self-tapping bone screws 44. In an important aspect of the present invention, the apertures 48 are carefully positioned on the plate 40 to avoid damaging the underlying extensor digitorum tendon 50 once the plate is placed on the finger. The positioning tube 42 depends downwardly at an angle from an aperture in the front portion of the plate 40. The tube 42 also protrudes slightly above the surface of the plate 40 to provide a stop for the threaded shoulder nut 62. The outside diameter of the tube 42 is slightly smaller than the inside diameter of the guide bore 18 to allow the tube 42 to be easily, yet snugly, inserted into the bore.

When fully inserted, the tube 42 extends across the spaced apart joint and into the distal phalanx 24. Advantageously, the fully inserted positioning tube 42 keeps the middle and distal phalanx 22, 24 in proper alignment and allows for easy and smooth insertion of the compression screw assembly 52. Additionally, the positioning tube 42 provides superior lateral stabilization of the joint during the critical healing period when fusion is taking place.

A compression screw assembly, generally designated by the reference numeral 52, is also provided with the kit. The screw assembly 52 includes a unique releasable anchor means 51 at its distal end that is particularly well-suited for use in small diameter bones, such as the phalanxes. As best seen in FIGS. 4 and 7, the screw assembly 52 comprises an elongated shaft 54 that is threaded over substantially its entire length, but includes smooth terminal shoulders 53, 55 at its distal and proximal ends, respectively. An end cap screw 61 threads into the distal end of the shaft 54 and allows convenient removal/replacement of the anchor means 51.

In the preferred embodiment of the anchor means 51, an end collar 57 is rotatably mounted on the shoulder 53 at the distal end of the screw shaft 54. A threaded lead nut 59 is spaced from the collar 57 on the threaded portion of the screw shaft 54. As best seen in FIG. 7, flexible prongs 63 extend radially around the periphery of both the collar 57 and the lead nut 59. The outer diameter of the prongs 63 is just slightly larger than the inner diameter of the guide bore 18, such that the prongs 63 gently engage the surrounding ossiferous surface of the bore 18. In this manner, when the screw shaft 54 is rotated to advance the lead nut 59, the prongs 63 provide sufficient frictional contact so that the lead nut 59 and the end collar 57 do not rotate. Advantageously, this frictional contact thus offsets the torsional component of the force generated by the threads of the screw shaft 54, leaving only the desired longitudinal component of the force to advance/retract the lead nut 59 on the shaft 54. Preferably, the prongs 63 are made of a resilient plastic or elastomeric material and embody sufficient flexibility to allow not only slight expansive movement, but also the required longitudinal movement, without significantly damaging the guide bore 18.

Positioned between the lead nut 59 and the collar 57 are two flat washers 65. The washers 65 provide attachment points for a plurality of flexible strands 67 that extend between the washers 65 in overlapping helices. Each strand 67 is prestressed into a spiral or helical shape and is fabricated from thin gauge stainless steel wire, or other suitably semi-flexible material.

In operation, the lead nut 59 is first installed on the end of the screw shaft 54 and advanced away from the collar 57 to retract the strands 67 and allow the entire screw assembly 52 to be inserted into the guide bore 18. Once inserted, the screw shaft 54 is rotated to advance the lead nut 59 toward the collar 57, thereby expanding the strands 67 outwardly to engage the surrounding bone. Advantageously, the spiral configuration of the expanded strands 67 provides continuous and secure contact with the surrounding bore 18 along substantially the entire length of each strand 67. In this manner, the screw assembly 52 is firmly anchored in the distal phalanx 24 to allow a strong and stable compressive force to be applied to the joint.

An alternative "narrow-profile" anchor means 51' is also provided. As shown in FIG. 7a, the alternative anchor means 51' comprises an extension screw 71 with a fixed head or collar 73 on its distal end and a non-threaded lead nut 75 that rotates freely about the screw 71. The alternative anchor means 51' is installed on the main screw shaft 54 by threading the proximal end of the screw 71 into a threaded hole in the distal shoulder 53 of the screw shaft 54. As the screw shaft 54 rotates and advances along the extension screw 71, it pushes the lead nut 75 toward the collar 73 to expand the enclosed strands 67' outwardly and engage the surrounding bone.

A significant advantage of the "narrow-profile" anchor means 51' is that the outside diameters of the lead nut 75 and the end collar 73 are the same, or slightly less than the diameter of the screw shaft 54. It follows that this "narrow-profile" design requires a guide bore 18 only slightly larger than the shaft 54. This allows the screw assembly 52 with the alternative anchor means 51' to be used in extremely small bones, such as in children, that would otherwise be too small.

The kit further includes an elongated shoulder nut 62 that is passed over the proximal shoulder 55 of the screw shaft 54 and rotated to engage the threaded portion of the shaft 54. As best seen in FIGS. 6 and 7, the nut 62 includes a tapered head 70 that abuts against the upper lip of the positioning tube 42. When the head 70 and the tube 42 are engaged, further rotation of the nut 62 advances the screw assembly 52 tending to pull the shaft 54 from the tube 42, and thus compresses the middle and distal phalanxes 22, 24 together. A combination tool 56 with the concentric drivers 58, 60 is used both to rotate the screw shaft 54 to expand/retract the anchor means 51, 51' and to install and tighten the shoulder nut 62 on the screw shaft 54.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with breadth to which they are fairly, legally and equitably entitled.

I claim:

1. A method of preparing and stabilizing a bone joint for fusion, adapted for the finger joints, comprising:

sawing a head of a first phalanx to form a first side of a miter joint;

drilling a guide bore through said first phalanx and longitudinally into a second phalanx;

smoothing an adjacent base of said second phalanx including use of the guide bore to form a second side of said miter joint for optimal knitting with said first side; and providing a compressive force along the axis of said guide bore to compress said first and said second phalanxes together;

whereby said first and second phalanxes are stabilized in compressive engagement for optimal fusion.

2. The method of preparing and stabilizing a bone joint for fusion of claim 1, further using a combination template having saw guide slots and a drill guide cylinder, an elongated bit to drill said guide bore, a reciprocating saw blade, a rotatable smoothing disk having a central guide post, a fixation plate having a positioning tube depending downwardly from said plate and a compression screw assembly, said method further comprising:

positioning said combination template over said joint;

moving said reciprocating saw blade downwardly within said guide slots to cut said head of said first phalanx to form said one side of said miter joint;

passing said bit through said guide cylinder and through said joint to form said guide bore;

rotating said smoothing disk against said adjacent base of said second phalanx to create said second side of said miter joint;

securing said fixation plate to the top of said finger with said positioning tube extending into said guide bore;

inserting said screw assembly through said positioning tube and into said guide bore;

anchoring said screw assembly near the distal end of said second phalanx; and engaging said screw assembly against said fixation plate to create said compressive force on said joint.

3. The method of preparing and stabilizing a bone joint for fusion of claim 2, wherein are further provided the steps of dislocating said second phalanx to one side and inserting said central guide post into said guide bore to position said disk at the desired angle with respect to said base prior to rotating said disk.

4. The method of preparing and stabilizing a bone joint for fusion of claim 2, wherein said step of anchoring further comprises rotating said screw assembly to expand anchor means at the distal end of said assembly to engage against surrounding bone within said bore.

5. The method of preparing and stabilizing a bone joint for fusion of claim 2, wherein said step of engaging said screw assembly against said plate further comprises threading an elongated shoulder nut onto the proximal end of said screw assembly to abut said plate, whereby further rotation of said nut tends to pull said screw assembly outwardly from said positioning tube to apply compressive force to said joint.

6. An instrument kit for preparing and stabilizing a bone joint for fusion, adapted for the finger joint of first and second phalanxes, comprising:
- a combination template including an elongated inverted channel having an upper face, parallel sides depending downwardly from said face, a drill guide means and a saw guide means;
- a guide bore bit having a shank for securement in a hand-held rotary drill;
- a saw blade with means for attaching to a reciprocating saw;
- a smoother to cooperate with a guide bore formed by said bit;
- an elongated fixation plate having a plurality of apertures;
- a compression screw assembly including an elongated and threaded shaft and a releasable anchor means at the distal end of said shaft for passing through one of said apertures and the first and second phalanxes and securing said assembly in the distal end of said second phalanx;
- a threaded shoulder nut for applying a force tending to pull said shaft outwardly from said guide bore to create a compressive force on said first and second phalanx joint; and
- driver tool means for rotating said screw assembly to operate said anchor means and for rotating said shoulder nut to secure said assembly.

7. The instrument kit of claim 6, wherein said drill guide means comprises an elongated cylinder extending upwardly from said one aperture in said upper face of said template, whereby said cylinder is adapted to receive said guide bore bit and directs said bit to drill a guide bore through said first phalanx and longitudinally into said second phalanx.

8. The instrument kit of claim 6, wherein said saw guide means comprises dual slots in said parallel sides of said template, said slots being open at their top end and having spaced edges to guide said saw blade to make a sheer cut through the head of said first phalanx.

9. The instrument kit of claim 6, wherein said drill guide means and said saw guide means are positioned on said template such that both said guide bore and said sheer cut are made without repositioning said template.

10. The instrument kit of claim 6, wherein said smoother includes a smoothing disk having a substantially flat circular surface having cutting protrusions extending outwardly therefrom.

11. The instrument kit of claim 10, wherein said disk further includes a cylindrical guide post extending from the center of said surface for insertion into said guide bore in said second phalanx to position said disk over the base of said second phalanx.

12. The instrument kit of claim 6, wherein said apertures in said fixation plate are positioned to allow the screw shaft and bone screws to be inserted into said finger without damaging underlying tendons in said finger.

13. The instrument kit of claim 12, wherein said fixation plate includes a positioning tube having an outside diameter smaller than the inside diameter of said guide bore, said tube depending downwardly at an angle from said screw assembly aperture and being open at both ends.

14. The instrument kit of claim 6, wherein said threaded shoulder nut comprises an elongated cylinder having internal threads for engaging the threads of said screw shaft and a tapered head at the top of said cylinder, whereby an angled head abuts against the protruding lip of said positioning tube and the rotation of said shoulder nut tends to pull said screw assembly outwardly from said guide bore to create said compressive force.

15. An instrument kit for preparing and stabilizing a bone joint for fusion, adapted for the finger joint of a first and second phalanxes, comprising:
- a combination template including an elongated inverted channel having an upper face, parallel sides depending downwardly from said face, a drill guide means and a saw guide means;
- a guide bore bit having a shank for securement in a hand-held rotary drill;
- a saw blade with means for attaching to a reciprocating saw;
- a rotatable smoothing disk having a shank for securement in a hand-held rotary drill;
- an elongated fixation plate having a plurality of apertures;
- a compression screw assembly including an elongated and threaded shaft and a releasable anchor means at the distal end of said shaft for passing through one of said apertures and the first and second phalanxes and securing said assembly in the distal end of said second phalanx, said releasable anchor means comprising a fixed collar rotatably engaged to a smooth shoulder at the distal end of said screw assembly, a threaded lead nut spaced from said collar on said shaft, a plurality of semi-flexible friction prongs extending outwardly from the peripheries of said collar and said lead nut to engage said guide bore and prevent the rotation of said nut and said collar, and a plurality of flexible strands extending in overlapping helices between said nut and said collar, whereby the rotation of said shaft advances said lead nut toward said collar and forces said strands to expand outwardly in a helical fashion into the surrounding bone to secure said assembly inside said guide bore;
- a threaded shoulder nut for applying a force tending to pull said shaft outwardly from said guide bore to create a compressive force on said first and second phalanx joint; and
- a dual function driver tool for rotating said screw assembly to operate said anchor means and for rotating said shoulder nut to secure said assembly.

16. An instrument kit for preparing and stabilizing a bone joint for fusion, adapted for the finger joints, comprising:
- a combination template including an elongated inverted channel having an upper face, parallel sides depending downwardly from said face, a drill guide means and a saw guide means;
- a guide bore bit having a shank for securement in a hand-held rotary drill;
- a saw blade with means for attaching to a reciprocating saw;
- a rotatable smoothing disk having a shank for securement in a hand-held rotary drill;

an elongated fixation plate having a plurality of apertures;

a compression screw assembly including an elongated and threaded shaft and a releasable anchor means at the distal end of said shaft for passing through one of said apertures and the first and second phalanxes and securing said assembly in the distal end of said second phalanx, said anchoring means comprising an extension screw having a fixed collar at its distal end, a non-threaded lead nut spaced from said collar on said shaft, a plurality of semi-flexible friction prongs extending outwardly from the peripheries of said fixed collar and said non-threaded lead nut to engage said guide bore and prevent the rotation of said nut and said collar, and a plurality of flexible strands extending in overlapping helices between said nut and said collar, whereby the proximal end of said extension screw threads into the distal end of said screw shaft and the rotation of said shaft pushes said lead nut toward said collar and forces said strands to expand outwardly in a helical fashion into the surrounding bone to secure said assembly inside said guide bore;

a threaded shoulder nut for applying a force tending to pull said shaft outwardly from said guide bore to create a compressive force on said first and second phalanx joint; and a dual function driver tool for rotating said screw assembly to operate said anchor means and for rotating said shoulder nut to secure said assembly.

\* \* \* \* \*